United States Patent
Yamamoto

(10) Patent No.: US 8,596,324 B2
(45) Date of Patent: Dec. 3, 2013

(54) WEB CONVEYING APPARATUS AND WEB CONVEYING METHOD

(75) Inventor: Hiroki Yamamoto, Kagawa (JP)

(73) Assignee: Unicharm Corporation, Ehime-Ken (JP)

( * ) Notice: Subject to any disclaimer, the term of this patent is extended or adjusted under 35 U.S.C. 154(b) by 0 days.

(21) Appl. No.: 13/383,889

(22) PCT Filed: Jul. 30, 2010

(86) PCT No.: PCT/JP2010/062944
§ 371 (c)(1),
(2), (4) Date: Mar. 21, 2012

(87) PCT Pub. No.: WO2011/013822
PCT Pub. Date: Feb. 3, 2011

(65) Prior Publication Data
US 2012/0178609 A1    Jul. 12, 2012

(30) Foreign Application Priority Data

Jul. 31, 2009 (JP) ................................. 2009-180203

(51) Int. Cl.
*B31F 1/00* (2006.01)
(52) U.S. Cl.
USPC ........... 156/461; 156/199; 156/204; 156/227; 156/229; 156/443; 156/459; 156/494; 156/496
(58) Field of Classification Search
USPC ......... 156/204, 227, 229, 494, 496, 461, 465, 156/468, 73.1, 199, 200, 201, 250, 269, 156/443, 459, 464, 497, 538; 226/196.1; 493/416, 436, 438, 439, 440, 442, 443, 493/446

See application file for complete search history.

(56) References Cited

U.S. PATENT DOCUMENTS

| 5,626,711 A | * | 5/1997 | Herrmann | 156/496 |
| 5,879,500 A | * | 3/1999 | Herrin et al. | 156/204 |
| 6,913,664 B2 | | 7/2005 | Umebayashi et al. | |

(Continued)

FOREIGN PATENT DOCUMENTS

| EP | 1504738 | 2/2005 |
| JP | 2003038566 A | 2/2003 |

(Continued)

OTHER PUBLICATIONS

International Search Report and Written Opinion for PCT/JP20101062944 dated Nov. 2, 2010.

(Continued)

*Primary Examiner* — John Goff
*Assistant Examiner* — Hannuri L Kwon
(74) *Attorney, Agent, or Firm* — Lowe Hauptman & Ham, LLP

(57) ABSTRACT

A web conveying apparatus configured to convey a pair of webs folded in the cross direction CD with reference to a folding line. The web conveying apparatus includes a crotch hold bar configured to hold an intermediate web in a conveyable manner with the folded intermediate web stretched in a direction in which the crotch portions get away from the waistline portions; and a conveying mechanism configured to convey the intermediate web and hands over the intermediate web to a joint apparatus and a cutting apparatus, while the crotch portions are being held by the crotch hold bar.

19 Claims, 10 Drawing Sheets

(56) References Cited

U.S. PATENT DOCUMENTS

| | | |
|---|---|---|
| 6,926,654 B2 | 8/2005 | Yamamoto et al. |
| 7,060,142 B2 | 6/2006 | Yamamoto |
| 7,144,357 B2 * | 12/2006 | Yamamoto et al. ............ 493/34 |
| 8,273,003 B2 | 9/2012 | Umebayashi et al. |
| 2004/0064121 A1 | 4/2004 | Van Gompel et al. |
| 2010/0050411 A1 | 3/2010 | Yamamoto |
| 2010/0179042 A1 | 7/2010 | Yamamoto |

FOREIGN PATENT DOCUMENTS

| | | |
|---|---|---|
| JP | 2004298413 A | 10/2004 |
| JP | 2005046246 | 2/2005 |
| JP | 2005046246 A | 2/2005 |
| JP | 2008174328 A | 7/2008 |
| JP | 2010227545 A | 10/2010 |
| WO | 2008142946 | 11/2008 |
| WO | 2010024373 A1 | 3/2010 |
| WO | 2010101277 | 9/2010 |
| WO | 2010101284 | 9/2010 |

OTHER PUBLICATIONS

Supplementary European Search Report issued May 22, 2013 corresponding to EP Patent application No. 10804568.3.

Office Action mailed Jun. 4, 2013 corresponding to Japanese patent application No. 2009-180203.

* cited by examiner

WEB CONVEYING APPARATUS AND WEB CONVEYING METHOD

RELATED APPLICATIONS

The present application is a National Phase of International Application Number PCT/JP2010/062944, filed Jul. 30, 2010 and claims priority from Japanese Application Number 2009-180203, filed Jul. 31, 2009.

TECHNICAL FIELD

The present invention relates to a web conveying apparatus and a web conveying method for conveying a web for an absorbent article including waistline portions and a crotch portion while folding the web in a cross direction orthogonal to a machine direction with reference to a folding line parallel with the machine direction on the crotch portion.

BACKGROUND ART

An absorbent article such as a pants-type disposable diaper and the like generally includes such members as waistline portions for the wearer's waistline (specifically, a front waistline portion and a back waistline portion), a crotch portion for the wearer's crotch, and an absorber which absorbs excretion discharged from the wearer. The pants-type diaper is provided with leg-surrounding portions where openings for inserting wearer's legs are formed. Each of the leg-surrounding portions is provided with a leg gather formed with a string-like rubber to fit the leg-surrounding portion to the wearer.

In a manufacturing process of such a pants-type diaper, a web including a continuum of the members described above is conveyed using conveying belts and the like. In a web folding step, a web is folded into two in the cross direction CD orthogonal to the machine direction MD so that a continuum of front waistline portions and a continuum of back waistline portions can be overlaid one another, while the web is being conveyed in the machine direction MD, that is, in a flow direction of the manufacturing process (Patent Document 1, for example). In this step, the front waistline portions and the back waistline portions are overlaid one another with reference to a folding line parallel with the machine direction on a non-continuum of the crotch portions discontinuously provided between a continuum of the front waistline portions and the back waistline portions (near a center, for example).

Next, in a web joining step, the front waistline portions are joined to the back waistline portions at a predetermined intervals by using a joint apparatus provided with a ultrasonic horn, while the web folded in two are continuously being conveyed in the machine direction (Patent Document 2, for example). Then, in a cutting step, the web is cut into individual pants-type diapers by using a cutting apparatus provided with a cutting blade.

In the web folded into two, the crotch portions are discontinuously provided in the machine direction, and are therefore conveyed by following conveyance of the continua of the front waistline portions and the back waistline portions. Also, in the web folded into two, a leg gather is provided on each of the leg-surrounding portions.

Accordingly, if no restrictions are applied to the web, there is a problem that the non-continuum of the crotch portions is likely to contract in a direction toward the continua of the front waistline portions and the back waistline portions, and in particular, the vicinity of the leg-surrounding portions provided with the leg gathers is likely to contract in a direction toward the continua of the front waistline portions and the back waistline portions.

In order to prevent the web from having creases due to contraction, a belt conveyor for conveying the web employs a suction belt configured to attract the web by means of the suction power. However, there is a problem that a defect such as a crease is likely to occur on the web since the web gets away from the belt conveyor at locations where the web is handed over from a belt conveyor to another apparatus (for example, the joint apparatus or the cutting apparatus described above).

PRIOR ART DOCUMENT

Patent Document

Patent Document 1: Japanese patent application publication No. 2005-46246 (Pages 6 and 7 and FIG. 3)
Patent Document 2: Japanese patent application publication No. 2004-298413 (Pages 9 and 10 and FIG. 5 and FIG. 6)

SUMMARY OF INVENTION

A web conveying apparatus according to a first aspect is configured to convey a web for an absorbent article folded into two in a cross direction orthogonal to the machine direction with reference to a folding line parallel with the machine direction on a crotch portion. The absorbent article includes: paired waistline portions which are continuous in the machine direction along a flow direction of a manufacturing process for an absorbent article; and crotch portions which are discontinuous in the machine direction and located between the paired waistline portions. The web conveying apparatus includes: a hold mechanism configured to hold the web in a conveyable manner with the web stretched in a direction in which the crotch portions get away from the waistline portions; and a conveying mechanism configured to convey the web and hands over the web to a downstream apparatus provided downstream in the machine direction, while the crotch portions are being held by the hold mechanism.

DESCRIPTION OF EMBODIMENTS

Next, embodiments of a web conveying apparatus and a web conveying method according to the present invention are described referring to the accompanying drawings. In the description of drawings hereinafter, same or similar signs are assigned to same or similar members. Note that the drawings are schematic and ratios of dimensions and the like are different from actual ones.

Therefore, specific dimensions and the like should be determined referring to the description given hereinafter. Moreover, the drawings also include portions having different dimensional relationships and ratios from each other.

Figure 1:
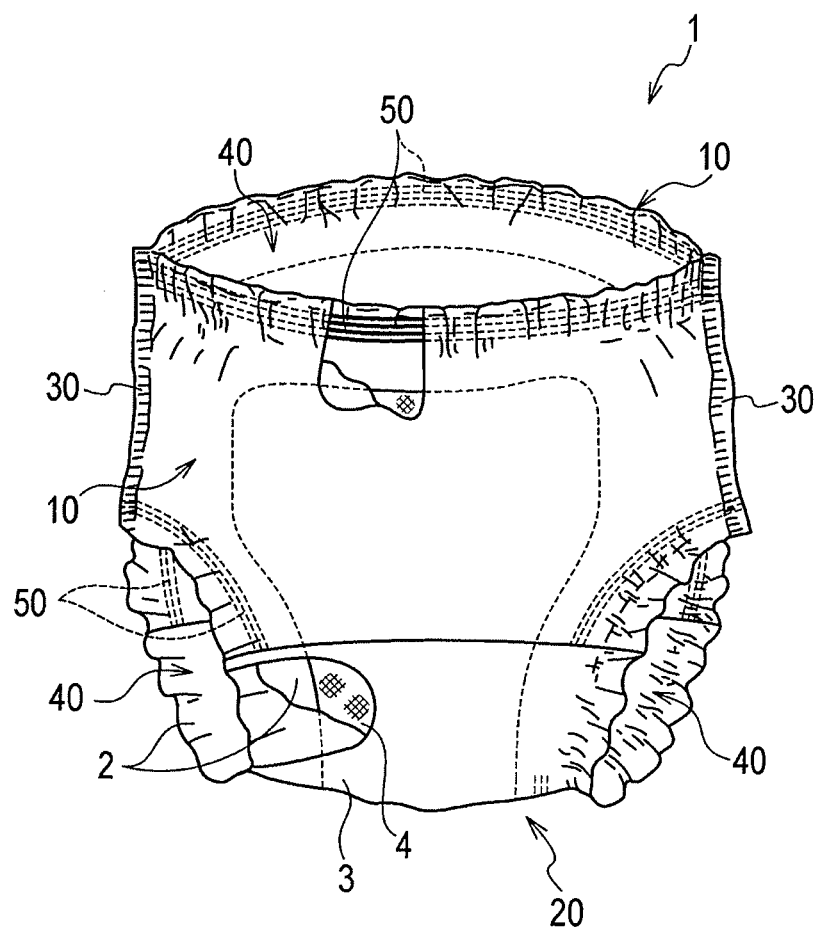
FIG. 1 is a perspective view showing an absorbent article 1 according to this embodiment.

First, with reference to the drawings, description will be provided for a configuration of an absorbent article 1 manufactured by a web conveying apparatus and a web conveying method according to the present invention. FIG. 1 is a perspective view showing the absorbent article 1 according to this embodiment.

According to this embodiment, the absorbent article 1 is a disposable pants-type diaper. As shown in FIG. 1, the absorbent article 1 mainly comprises a topsheet 2, a backsheet 3 and an absorber 4.

The topsheet 2 is provided at an innermost portion of the absorbent article 1 in contact with wear's skin The topsheet 2 is a liquid permeable sheet made of a nonwoven fabric or a perforated plastic film, or the like. The backsheet 3 is provided at an outermost portion (on a side away from the wearer) of the absorbent article 1. The backsheet 3 is a liquid permeable sheet or the like. The absorber 4 is provided between the topsheet 2 and the backsheet 3 so as to absorb excretion discharged from the wearer. The absorber 4 is made of a mixture of ground pulp and superabsorbent polymer particles, and the like.

Such absorbent article 1 includes a pair of waistline portions 10 (a front waistline portion and a back waistline portion) to be fitted to the wearer's waistline and a crotch portion 20 to be fitted to the wearer's crotch. The waistline portions 10 are joined together on sides of the wearer's waistline by a joint portion 30.

The absorbent article 1 is provided with multiple openings 40 (a waistline opening portion and leg-surrounding opening portions). A gather 50 formed using a string-like rubber is provided around an entire peripheral edge of each of the openings 40.

Figure 2:
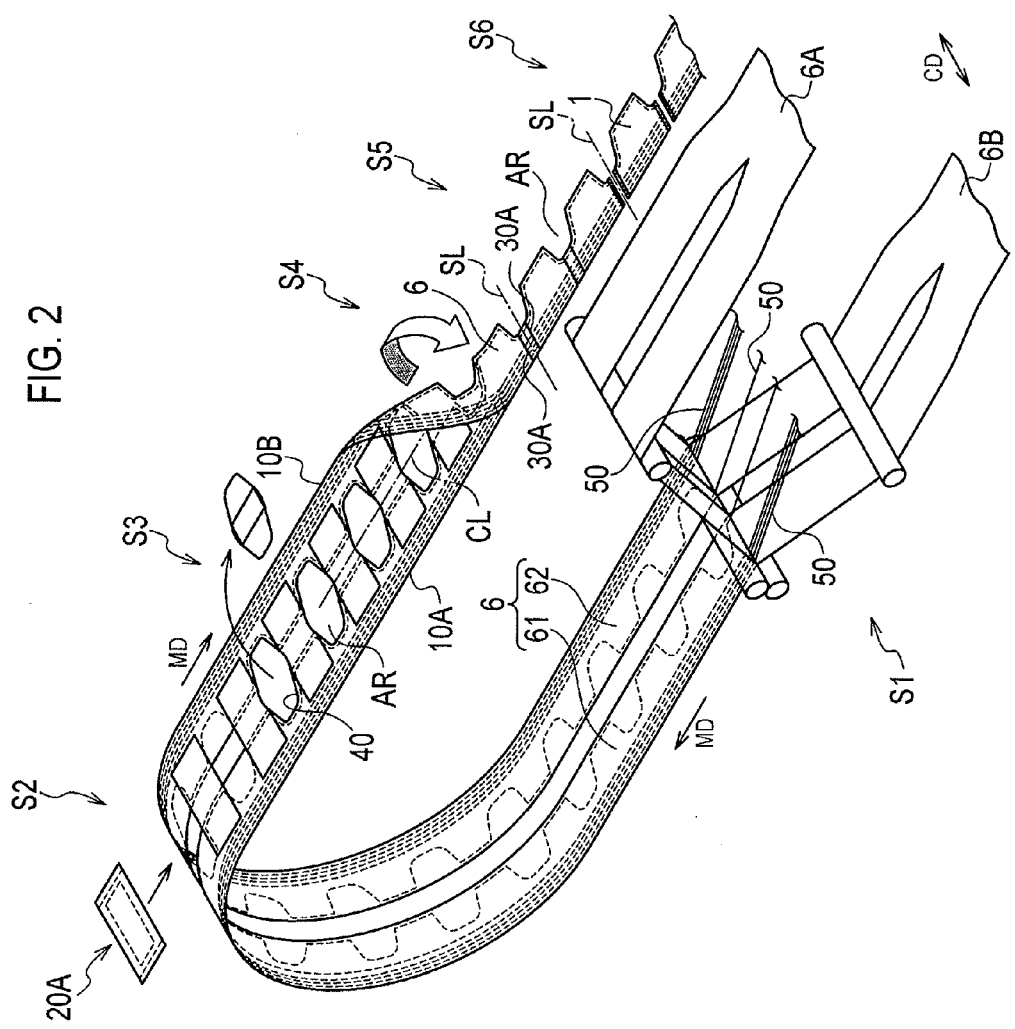
FIG. 2 is a drawing for partially illustrating a method for manufacturing the absorbent article 1 according to this embodiment.

Next, a method for manufacturing an absorbent article 1 according to this embodiment is described referring to the accompanying drawings. FIG. 2 is a drawing for partially illustrating the method for manufacturing an absorbent article 1 according to this embodiment.

As shown in FIG. 2, the method for manufacturing an absorbent article 1 includes at least a waistline portion forming step S1, a crotch portion transferring step S2, a leg-surrounding portion forming step S3, a folding step S4, a joining step S5 and a cutting step S6.

In the waistline portion forming step S1, gathers 50 are placed between a web 6A and a web 6B so as to form a pair of webs 61 and 62 respectively corresponding to the pair of waistline portions 10.

Provided with the leg gather 50, the webs 61 and 62 (webs 6A and 6B) can contract (extend) in a cross direction CD orthogonal to the machine direction MD along a flow direction of a manufacturing process for the absorbent article 1. Moreover, the webs 61 and 62 pass a center in the machine direction MD and are asymmetrical each other with reference to a center line CL along the machine direction MD.

In the crotch portion transferring step S2 following (downstream of) the waistline portion forming step S1, a crotch portion member 20A to be fitted to the crotch portion 20 is transferred (disposed) between the pair of webs 61 and 62 at a predetermined intervals along the machine direction MD.

In the leg-surrounding portion forming step S3 following (downstream of) the crotch portion transferring step S2, a portion of the backsheet 3 made into the webs 61 and 62 (webs 6A and 6B) and the crotch portion member 20A is cut. An airspace AR is formed by the waistline opening portion to be fitted to one absorbent article 1 and another the waistline opening portion to be fitted to another absorbent article 1 close to the absorbent article 1.

In the folding step S4 (downstream) following the leg-surrounding portion forming step S3, a pair of webs 61 and 62 is folded in the cross direction CD with reference to a folding line on the crotch member 20A parallel with the machine direction MD. Specifically, a side edge 10A of one web 61 and a side edge 10B of the other web 62 are folded into two by aligning with each other in a predetermined positional relationship with reference to the folding line, whereby an intermediate web 6 is obtained. At this time, an airspace AR becomes of a semicircle-like shape in a plan view of the folded intermediate web 6.

According to this embodiment, the folding line is the center line CL which passes a center of the intermediate web 6 in the cross direction CD and extends toward the machine direction MD. Moreover, the folding line may not necessarily be the center line CL, but may be shifted from the center line CL toward the side edge 10A or the side edge 10B.

In the joining step S5 following (downstream of) the folding step S4, a joint apparatus 200 (refer to FIG. 6) described later performs joining on a joint region 30A to be formed into the joint portion 30 where the pair of waistline portions 10 are joined together. The joint regions 30A are formed respectively on both sides of an imaginary line SL indicating an intended cutting position extending in the cross direction CD of the intermediate web 6.

In the cutting step S6 following (downstream of) the joining step S5, intermediate webs 6 joined at the joint area 30A are cut at predetermined intervals in the machine direction MD, that is, along the imaginary line SL, whereby individual absorbent articles 1 are manufactured.

Here, the folding step S4 described above is followed by steps of a web conveying method according to this embodiment. The web conveying method is configured to convey a pair of folded webs 61 and 62 using a web conveyor 100 (refer to FIG. 3 and FIG. 4) described later. The web conveying method includes a web holding step and a web handover step.

In the web holding step, a pair of folded webs 61 and 62 are held and conveyed by using a crotch hold bar 110 included in a web conveyor 100, while the web 61 is being stretched in a direction in which the crotch member 20A gets away from the waistline portions (that is, in the cross direction CD).

In the web handover step, by using a conveying mechanism 120 included in the web conveyor 100, the web 61 is conveyed and handed over to a downstream apparatus (for example, the joint apparatus 200 or the cutting apparatus 300) provided downstream of the manufacturing process, while the crotch member 20A is held by the crotch hold bar 100.

Figure 3:
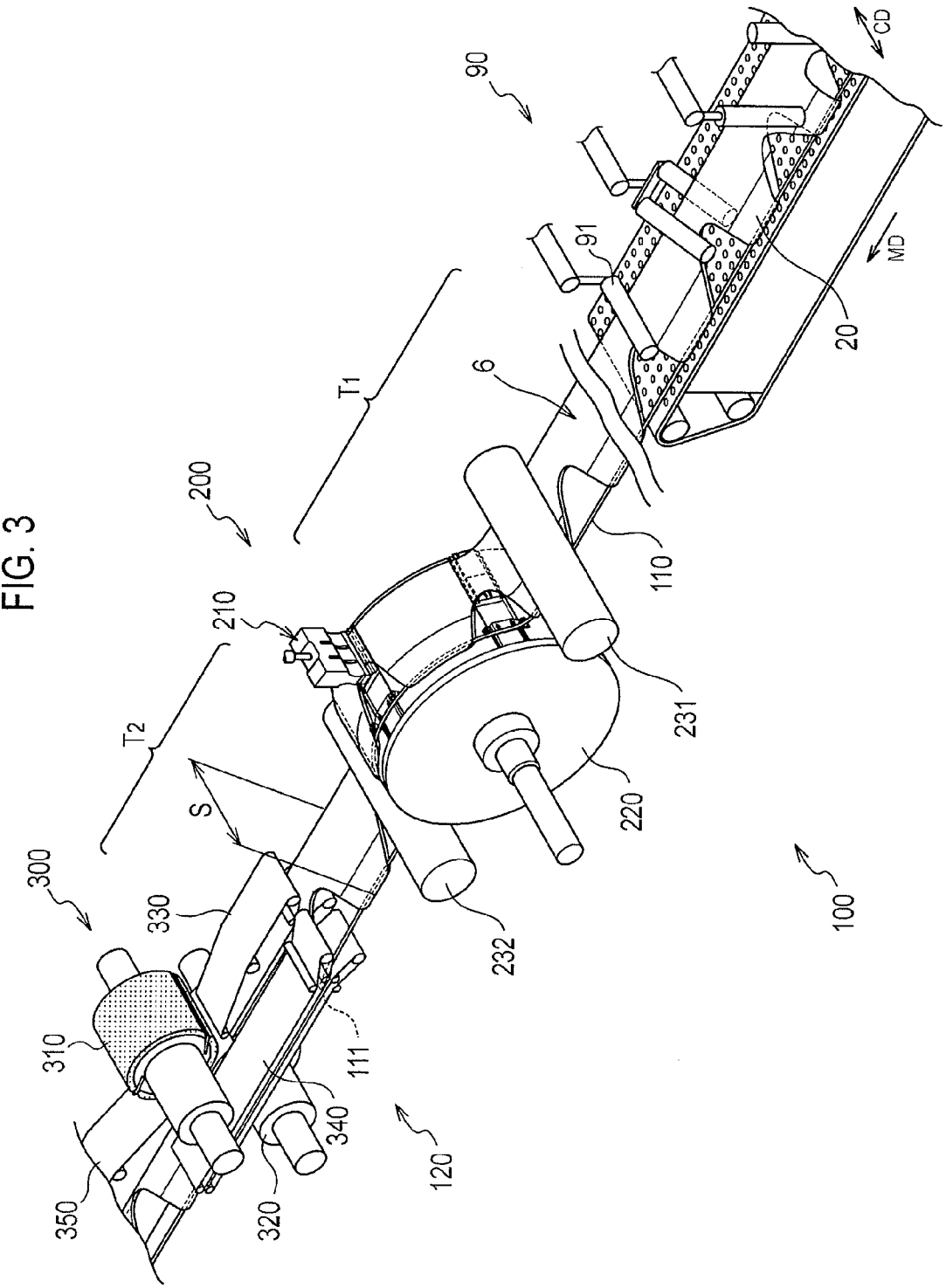
FIG. 3 is a perspective view showing a portion of a web conveyor 100 according to this embodiment.

Next, a configuration of the web conveyor 100 according to this embodiment is described referring to the accompanying drawings. FIG. 3 is a perspective view showing a portion of the web conveyor 100 (a folding apparatus 90, a joint apparatus 200 and a cutting apparatus 300) according to this embodiment.

Figure 4:
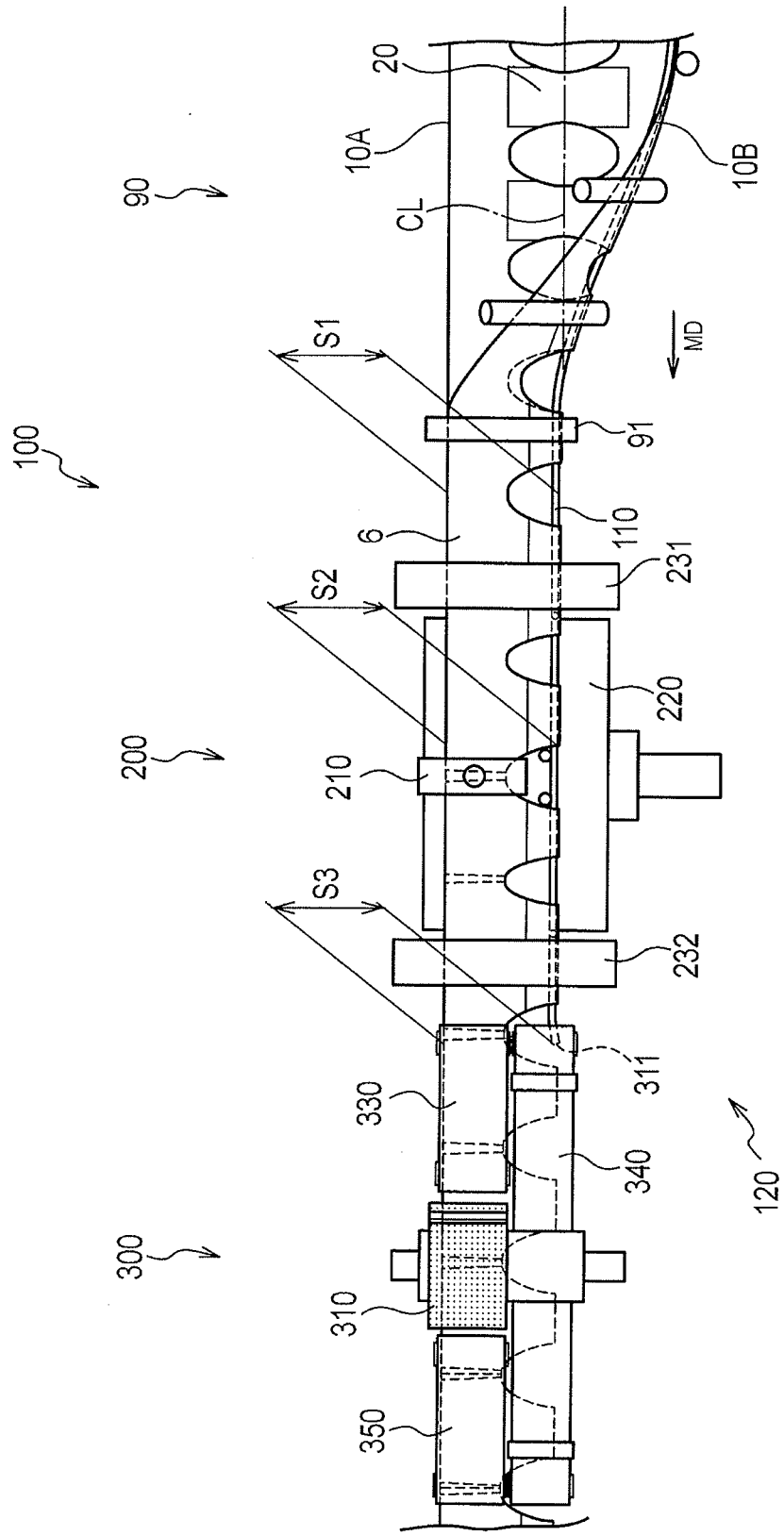
FIG. 4 is a plan view showing a portion of the web conveyor 100 according to this embodiment.
Figure 5:
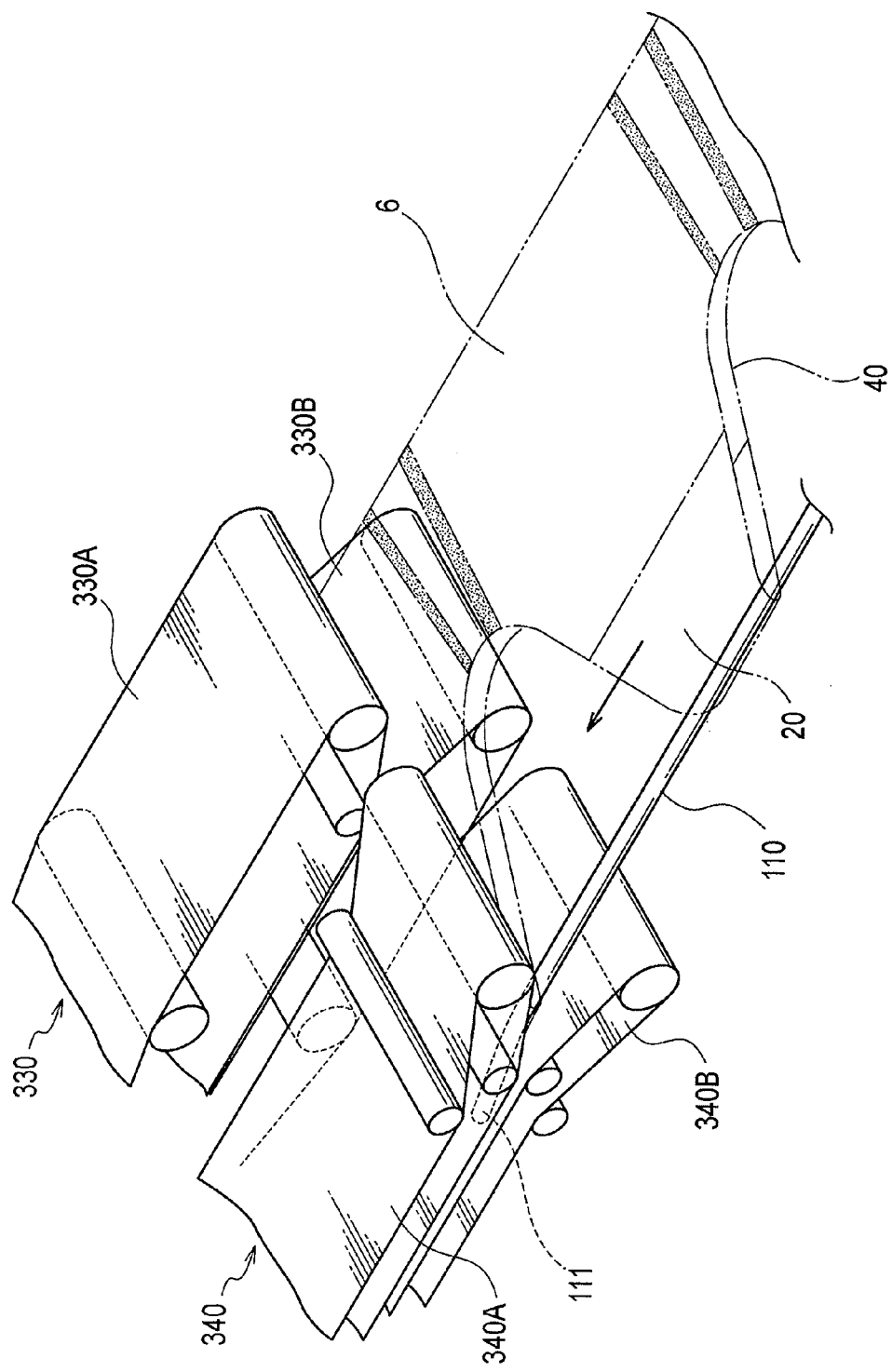
FIG. 5 is a perspective view showing the vicinity of an edge 111 of a crotch hold bar 110 according to this embodiment.

FIG. 4 is a plan view showing a portion of the web conveyor 100 according to this embodiment. FIG. 5 is a perspective view showing the vicinity of an edge 111 of the crotch hold bar 110 according to this embodiment.

As shown in FIG. 3 and FIG. 4, the web conveyor 100 is provided at least downstream of the folding apparatus 90 used in the folding step S4. The web conveyor 100 conveys the intermediate web 6, more specifically, a pair of webs 61 and 62 folded in the cross direction CD with reference to the folding line. The web conveyor 100 includes the crotch hold bar 110 (hold mechanism) and the conveying mechanism 120.

The crotch hold bar 110 holds the intermediate web 6, in a conveyable manner with the intermediate web 6 stretched in a direction in which the crotch member 20 gets away from the waistline portions, i.e., in the cross direction. The crotch hold bar 110 holds the stretched intermediate web 6 so as not to allow contraction of the intermediate web 6.

Displacement of the crotch hold bar 110 along the cross direction CD is restricted (held) by a restricting unit 500 described later. The crotch hold bar 110 stretches the folded intermediate web 6 from the inside of the crotch member 20A thereof.

The crotch hold bar 110 is provided at a position where the intermediate web 6 can be stretched from the inside of the crotch member 20A, which guides the intermediate web 6 slidably. The inside of the crotch member 20A represents a section between a part of a topsheet 2 on one of the waistline portion 10 and a part of the topsheet 2 on another one of the waistline portion 10, when a pair of the webs 61 and 62 is folded in two parts.

Such crotch hold bar 110 is provided at least at a region T1 including a location where the intermediate web 6 is handed over from the folding step S4 to the joining step S5, and at a region T2 including a location where the intermediate web 6 is handed over from the joining step S5 to the cutting step S6.

According to this embodiment, the crotch hold bar 110 exists from a location where folding of a pair of webs 61 and 62 is finished in the folding step S4 (by the folding apparatus 90) to the joint apparatus 200 used in the joining step S5. Also, the crotch hold bar 110 exists from a location where joining of a pair of the waistline portions 10 is finished in the joining step S5 to the cutting apparatus 300 used in the cutting step S6.

According to this embodiment, the crotch hold bar 110 is configured by extension of a folding guide bar up to a non-continuum conveying mechanism 340, the folding guide bar included in the folder 90. Specifically, the edge 111 of the crotch hold bar on a side of the cutting apparatus 300 extended by the folding guide bar extends up to the non-continuum conveying mechanism 340 at the cutting apparatus 300 as shown in FIG. 5. Meanwhile, the folding guide bar extends on the folding line along the mechanical direction MD so as to press a base point where one web 61 and another web 62 are folded each other.

The crotch hold bar 110 has a rod-like member extending along the machine direction MD. Cross section of the crotch hold bar in a lateral direction has a circular shape. The crotch hold bar 110 is formed with a metal material and coated with a coating material made of fluorine resin (for example, a tube made of the polytetrafluoroethylene).

As shown in FIG. 3, a distance S from en edge (side edge 10A or side edge 10B) of the waistline portions 10 in the cross direction CD of the intermediate web 6 to an outer edge of the crotch hold bar 110 in the cross direction CD is longer when the crotch hold bar 110 hands over the intermediate web 6 to a downstream apparatus (joint apparatus 200 or cutting apparatus 300) than when the intermediate web 6 is being conveyed. In particular, as shown in FIG. 4, assume that the distance S includes a distance S1 in the folding step S4, a distance S2 in the joining step S5 and a distance S3 in the cutting step S6. Those distances preferably have a relationship of S1≤S2≤S3.

The conveying mechanism 120 conveys the folded intermediate web 6 with the crotch member 20A held by the crotch hold bar 110 and hands over the intermediate web 6 to the joint apparatus 200 and the cutting apparatus 300, provided downstream of the manufacturing process.

According to this embodiment, the conveying mechanism 120 may be a guide roll 91 included in the folding apparatus 90, a rotary drum 220 in the joint apparatus 200 described later or a guide roll 230, or a continuum conveying mechanism 330 in the cutting apparatus 300. Obviously, the conveying mechanism 120 also may be of a configuration capable of conveying the web 61 under tension along the machine direction MD (for example, a driving roll).

Figure 6:
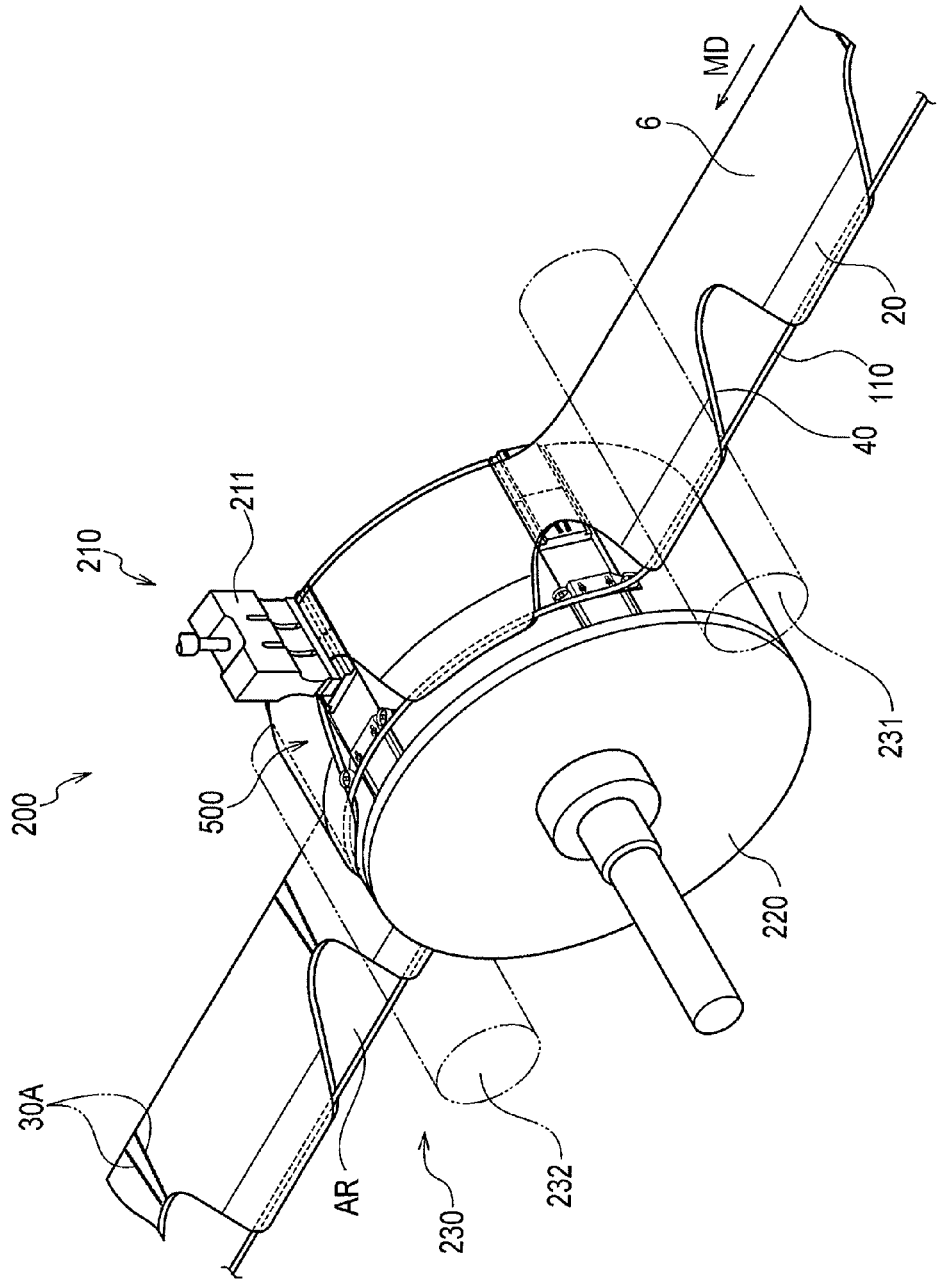
FIG. 6 is a perspective view showing a joint apparatus 200 according to this embodiment.

Next, a configuration of the joint apparatus 200 according to this embodiment is described referring to a drawing. FIG. 6 is a perspective view showing the joint apparatus 200 according to this embodiment.

As shown in FIG. 6, the joint apparatus 200 is located downstream of the folding apparatus 90 (refer to FIG. 3 and FIG. 4) used in the folding step S4. The joint apparatus 200 forms the joint portion 30 on the intermediate web 6 by joining the joint region 30A to be formed into the joint portion 30. The joint apparatus 200 includes an ultrasonic mechanism 210, a rotary drum 220 and a guide roll 230.

The ultrasonic mechanism 210 applies ultrasonic vibration to the joint region 30A of the intermediate web 6 by holding the joint region 30A in coordination with an anvil roll 222 in the rotary drum 220 described later. The ultrasonic mechanism 210 includes at least an ultrasonic horn 211 which joins the joint region 30A to be formed into the joint portion 30. The ultrasonic horn 211 applies ultrasonic vibration oscillated from an ultrasonic vibrator (not shown) to the joint region 30A by contacting the anvil roll 222 beyond the intermediate web 6 so as to join the joint region 30A.

The rotary drum 220 conveys the intermediate web 6 toward the machine direction MD while supporting the intermediate web 6. The rotary drum 220 is provided with multiple anvil rolls 222 fixed at concave portions 221 (refer to FIG. 7) recessed from an outer peripheral surface of the rotary drum 220. The anvil rolls 222 face the ultrasonic horn 211 beyond the intermediate web 6, and the multiple anvil rolls (for example, five) are provided on an outer peripheral surface of the rotary drum 220 at a predetermined interval in the machine direction MD. The anvil rolls 222 project externally from the rotary drum 220.

Furthermore, the rotary drum 220 includes a restricting unit 500 which restricts a displacement along a cross direction of the crotch hold bar 110. Details of the restricting unit 500 are described later (refer to FIG. 7).

On a portion of the outer peripheral surface of the rotary drum 220, the crotch hold bar 110 described above is disposed. That is, the crotch hold bar 110 is disposed along a portion of the outer peripheral surface of the rotary drum 220. In an axial view of the rotary drum 220, the intermediate web 6 and the crotch hold bar 110 pass the outer peripheral surface of the rotary drum 220 located upstream.

A guide roll 230 supports the intermediate web 6 and the crotch hold bar 110 so that the intermediate web 6 and the crotch hold bar 110 are located along the outer peripheral surface of the rotary drum 220. The guide roll 230 opposes the rotary drum 220 beyond the intermediate web 6. The guide roll 230 includes an upstream roll 231 located upstream of the rotary drum 220 and a downstream roll 232 located downstream of the rotary drum 220.

Figure 7:
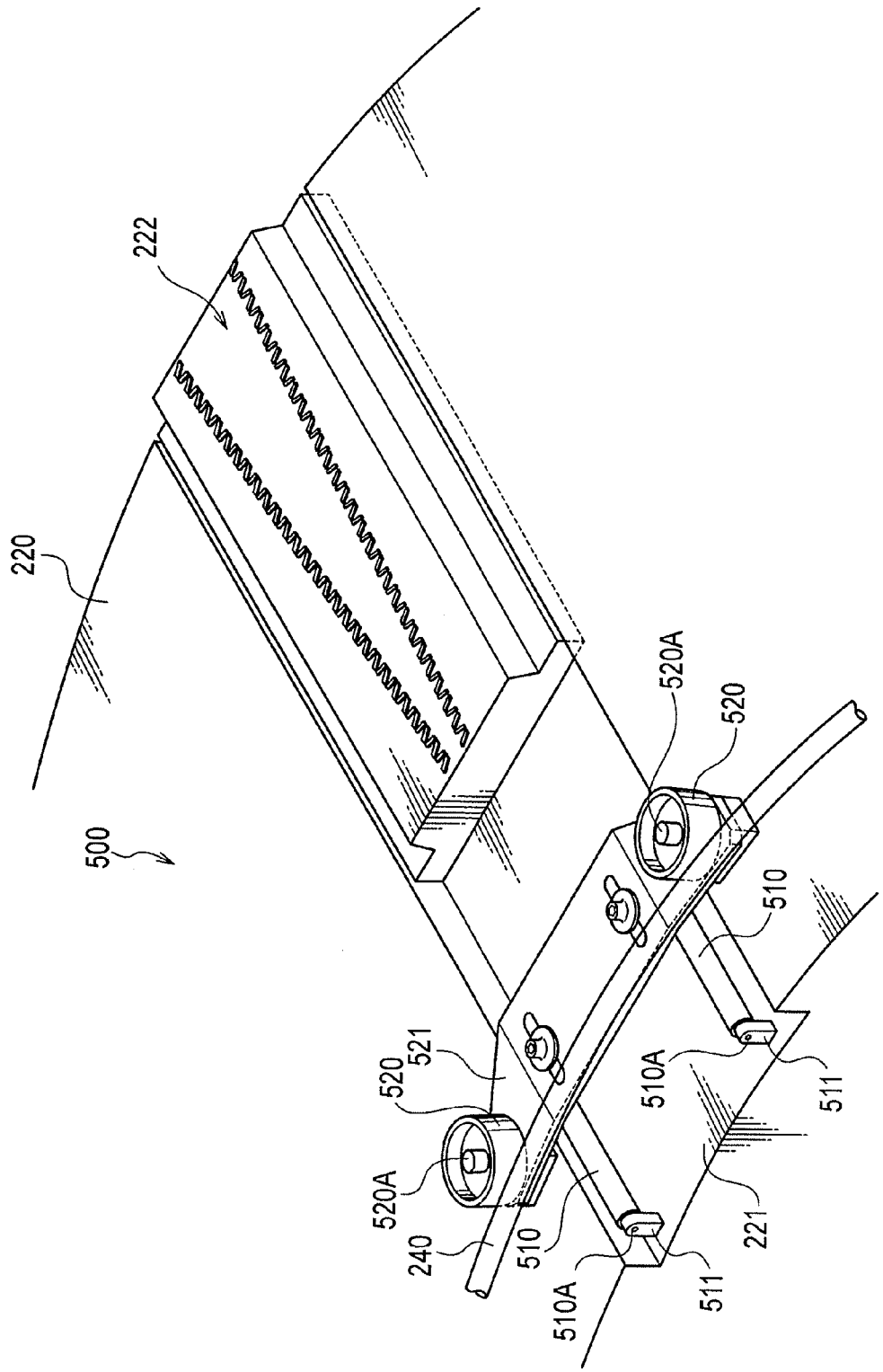
FIG. 7 is a perspective view showing the vicinity of a restricting unit 500 according to this embodiment.

Next, a configuration of the restricting unit 500 according to this embodiment is described referring to a drawing. FIG. 7 is a perspective view showing the vicinity of the restricting unit 500 according to this embodiment.

As shown in FIG. 7, the restricting unit 500 is provided on a portion of the outer peripheral surface of the rotary drum 220 and rotates together with the rotary drum 220. The multiple (for example, five) restricting units are provided in a circumferential direction of rotary drum 220 at same locations as the anvil rolls 222.

When the intermediate web 6 passes the outer peripheral surface of the rotary drum 220, the restricting unit 500 rotates at the position of the airspace AR disposed on the intermediate web 6 being conveyed (refer to FIG. 6). Specifically, the restricting unit 500 is located within an area from the crotch hold bar 110 to the waistline portions of the intermediate web 6. In particular, the restricting unit 500 is preferably provided close to a larger side in a semicircle-like space formed by the intermediate web 6 in a plan view of the intermediate web 6.

The restricting unit 500 includes a roller capable of rotating in the machine direction MD of the intermediate web 6 by coming into contact with the crotch hold bar 110. Specifically, the restricting unit 500 includes at least multiple first rollers and multiple second rollers 520.

A first roller 510 reduces friction between the rotary drum 220 and the crotch hold bar 110. The first roller 510 restricts a displacement of the crotch hold bar 110 along a vertical direction. The first roller 510 is supported by a frame 511 fixed to concave portions 221 of the rotary drum 220. The first roller 510 includes an axis 510A same as a shaft center of the rotary drum 220. The first roller 510 has a vertically long shape in the width direction of the rotary drum 220. The first roller 510 projects beyond the outer peripheral surface of the rotary drum 220. The first roller 510 rotates in contact with the rotary drum 220 at the crotch hold bar 110 when the rotary drum 220 rotates.

A second roller 520 restricts a displacement of the crotch hold bar 110 toward a side closer to the waistline portions 10 of the intermediate web 6, that is, a displacement along the cross direction CD. The second roller 520 is supported by a frame 521 fixed to the outer peripheral surface of the rotary drum 220. The second roller 520 includes an axis 520A along a direction crossing the shaft center of the rotary drum 220 at right angle (in a radial direction of the rotary drum 220). Width of the second roller 520 is set to be larger than the diameter of the crotch hold bar 110. The second roller 520 rotates in contact with the waistline portions 10 of the intermediate web 6 at the crotch hold bar 110.

Figure 8:
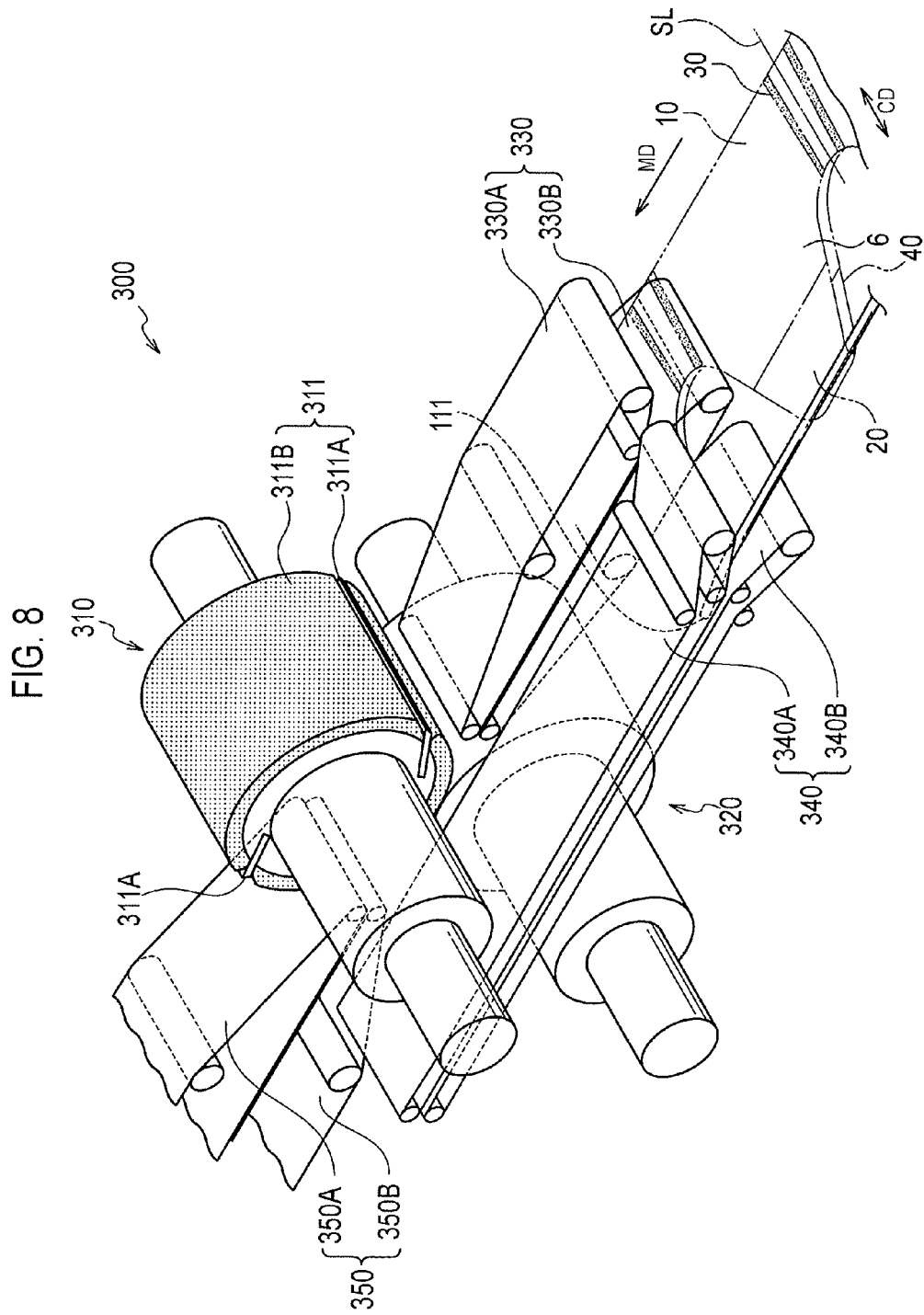
FIG. 8 is a perspective view showing a cutting apparatus 300 according to this embodiment.

Next, a configuration of the cutting apparatus 300 is described referring to a drawing. FIG. 8 is a perspective view showing the cutting apparatus 300 according to this embodiment.

As shown in FIG. 8, the cutting apparatus 300 is located downstream of the joint apparatus 200 and cuts the intermediate web 6 in which the joint portion 30 is formed, at a predetermined interval along the cross direction CD (along the imaginary line SL). The cutting apparatus 300 includes an upper blade 310, anvil rolls 320, a continuum conveying mechanism 330, a non-continuum conveying mechanism 340 and an article conveying mechanism 350.

The upper blade roll 310 includes multiple cutting blades 311A which cut the intermediate web 6 (that is, a continuum of waistline portions in the machine direction MD) along the imaginary line SL, and a hold member 311B which holds the intermediate web 6 by contacting the anvil rolls 320 beyond the intermediate web 6. On the other hand, the anvil roll 320 includes at least a bed knife (not shown) opposing the upper blade roll 310 beyond the intermediate web 6.

A continuum conveying mechanism 330 includes a pair of belt conveyors 330A and 330B provided upstream of the upper blade roll 310 and the anvil rolls 320. The non-continuum conveying mechanism 340 includes a pair of belt conveyors 340A and 340B provided between upstream and downstream of the upper blade roll 310 and anvil rolls 320. The article conveying mechanism 350 includes a pair of belt conveyors 350A and 350B provided downstream of the upper blade roll 310 and the anvil rolls 320.

Here, an edge 111 of the crotch hold bar 110 on the side of the cutting apparatus 300 is located between the pair of the belt conveyors 340A and 340B. The edge 111 of the crotch hold bar 110 is held between the pair of the belt conveyors 340A and 340B by the rigidity of the crotch hold bar 110.

According to the embodiment described above, the crotch hold bar 110 holds the intermediate web 6 in a conveyable manner with the web 61 stretched in a direction where the crotch member 20A gets away from the waistline portions, i.e., in the cross direction CD. Thus, the crotch hold bar 110 can suppress contraction of the web 61 (in particular, a vicinity of the leg-surrounding opening portions) in the cross direction CD even when a gather 50 is provided around an entire peripheral edge of the leg-surrounding opening portions.

Furthermore, the conveying mechanism 120 conveys the folded intermediate web 6 with the crotch member 20A held by the crotch hold bar 110 and hands over the folded intermediate web 6 to a downstream apparatus provided downstream of the manufacturing process, that is, the joint apparatus 200 and the cutting apparatus 300. Thus, the conveying mechanism 120 can hand over the intermediate web 6 to a downstream apparatus with the intermediate web 6 not contracted in the cross direction CD, whereby occurrence of a defect such as crease on the intermediate web 6 can be prevented more surely.

According to this embodiment, the edge 111 of the crotch hold bar 110 exists up to a downstream apparatus, that is, up to the joint apparatus 200 and the cutting apparatus 300. That is, the crotch hold bar 110 is configured by extension of the folding guide bar included in the folding apparatus 90 up to the non-continuum conveying mechanism 340. Thus, the folded intermediate web 6 can be surely handed over to the joint apparatus 200 or the cutting apparatus 300 with the intermediate web 6 (in particular, a vicinity of the leg-surrounding opening portions) not contracted in the cross direction CD. As a result, occurrence of a defect such as crease on the intermediate web 6 can be prevented more surely. Moreover, joining of the joint region 30A having a defect such as crease on the intermediate web 6 in the joining step S5 can be prevented and cutting of the intermediate web 6 having a defect such as crease thereon in the cutting step S6 can be prevented. Accordingly, manufacture defect of the absorbent article 1 can be reduced.

According to this embodiment, the crotch hold bar 110 stretches the folded intermediate web 6 from the inside of the crotch member 20A thereof. For example, when the intermediate web 6 is stretched by a belt conveyor holding the intermediate web 6 from the outside of the crotch member 20A, a defect such as crease may occur at the outside of the crotch member 20A (on the side of backsheet 3) between the outside of the crotch member 20A and the belt conveyor. However, if the crotch hold bar 110 stretches the intermediate web 6 from the inside of the crotch member 20A, the crotch hold bar 110 does not contact the outside of the crotch member 20A and a contact area between the crotch hold bar 110 and the intermediate web 6 becomes smaller, whereby a defect such as crease is unlikely to occur on the outside of the crotch member 20A.

According to this embodiment, a distance S from an edge (side edge 10A or side edge 10B) of the waistline portions 10 in the cross direction CD of the intermediate web 6 to an outer edge in the cross direction CD of the crotch hold bar 110 is longer when the crotch hold bar 110 hands over the intermediate web 6 to a downstream apparatus (joint apparatus 200 or cutting apparatus 300) rather than when the intermediate web 6 is conveyed. Moreover, when a distance S at the time of hand-over is shorter than a distance S during the conveyance, the intermediate web 6 (in particular, the vicinity of the leg-surrounding opening portions) is likely to contract in the cross direction CD, and thereby a defect such as crease resulting from contraction of the intermediate web 6 may not be suppressed.

Meanwhile, if a crotch member 20A (for example, the gather 50) is rubbed excessively by the crotch hold bar 110 during conveyance of the intermediate web 6, the crotch member 20A may be broken, the gather 50 may project beyond the leg-surrounding opening portion or an adhesive such as a hot melt may adhere to the crotch hold bar 110. However, since the distance S can be extended gradually according to conveyance of the intermediate web 6, possibility of occurrence of the defect described above can be minimized, and occurrence of a defect such as crease in the cutting step S6 as well as on a finished absorbent article 1 can be suppressed more surely.

In particular, assuming that the distance S includes a distance S1 in the folding step S4, a distance S2 in the joining step S5 and a distance S3 in the cutting step S6, it is preferably to satisfy the relationship of $S1 \leq S2 \leq S3$. Thus, when the intermediate web 6 is handed over to a downstream apparatus (for example, joint apparatus 200 or cutting apparatus 300), occurrence of crease or the like due to sudden pull of the intermediate web 6 may be suppressed more surely, whereby manufacture defect of the absorbent article 1 is reduced and appearance texture or the like of the absorbent article 1 may be improved.

According to this embodiment, the rotary drum 220 at the joint apparatus 200 includes the second roller 520 which restricts a displacement of the crotch hold bar 110 in the cross direction CD. When the intermediate web 6 passes an outer peripheral surface of the rotary drum 220, the second roller 520 is located at the airspace AR disposed on the intermediate web 6 by the waistline portions. Thus, even when the crotch hold bar 110 is forced to displace to a waistline portions side of the intermediate web 6 by a stress applied by contraction of the intermediate web 6 in the cross direction CD, the crotch hold bar 110 comes into contact with the restricting unit 500. That is, the crotch hold bar 110 is not unnecessarily displaced to a waistline portions side of the intermediate web 6. Consequently, the intermediate web 6 is held by the crotch hold bar 110 stretching along the cross direction CD, whereby occurrence of a defect such as a crease on the intermediate web 6 can be suppressed more surely.

Furthermore, the rotary drum 220 at the joint apparatus 200 includes the first roller 510 which restricts a displacement of the crotch hold bar 110 in the vertical direction. Thus, the crotch hold bar 110 contacts the first roller 510 without directly contacting an outer peripheral surface of the rotary drum 220. Consequently, friction between the rotating rotary drum 220 and the not-rotating crotch hold bar 110 is reduced, whereby occurrence of a defect such as crease on the intermediate web 6 can be suppressed more surely without rotation of the rotary drum 220 being interfered by the crotch hold bar 110.

According to this embodiment, the crotch hold bar 110 is provided at the region T1 including a location where the intermediate web 6 is handed over from the folding step S4 to the joining step S5. Thus, the intermediate web 6 can be handed over to the joint apparatus surely with the intermediate web 6 (in particular, the vicinity of the leg-surrounding opening portions) not contracting in the cross direction CD, whereby occurrence of a defect such as crease on the intermediate web 6 can be suppressed more surely, and in the joining step S5, joining of the joint region 30A to the intermediate web 6 having a defect such as crease can be prevented.

According to this embodiment, the crotch hold bar 110 is provided at the region T2 including a location where the web 61 is handed over from the joint step S5 to the cutting step S6. Thus, the intermediate web 6 can be surely handed over to the cutting apparatus 300 with the intermediate web 6 (in particular, a vicinity of the leg-surrounding opening portions) not contracting in the cross direction CD. This can even more surely prevent occurrence of a defect such as crease on the intermediate web 6, and therefore can prevent cutting of the intermediate web 6 having a defect such as crease in the joining step S5.

MODIFIED EMBODIMENT

Figure 9:
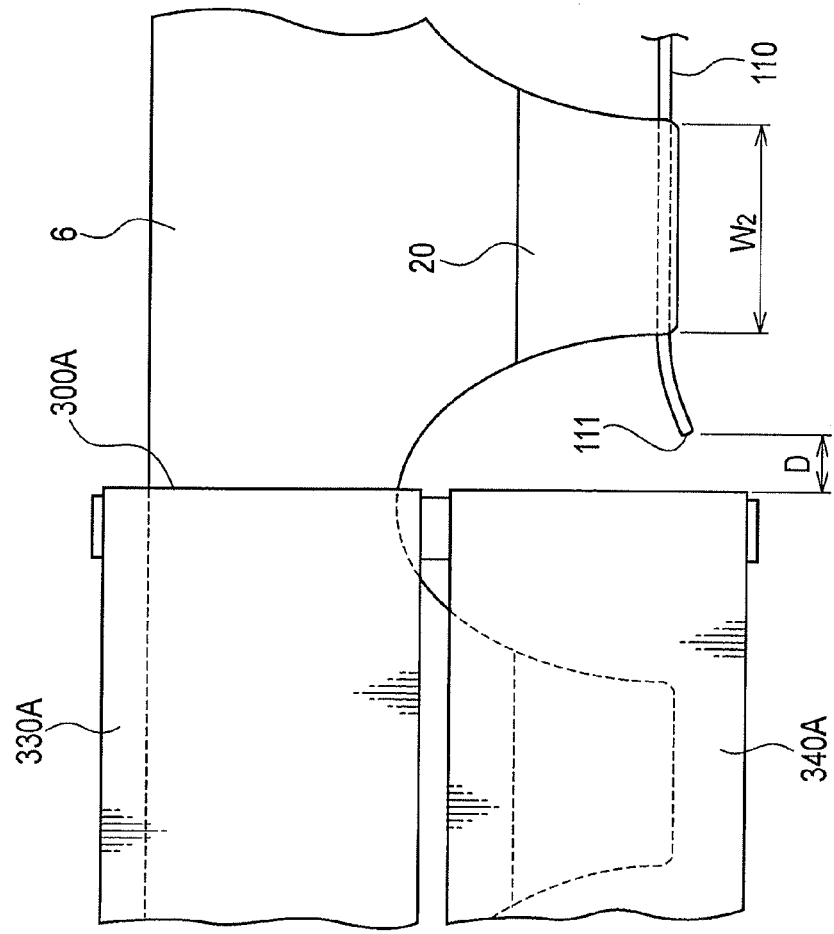
FIG. 9 is a perspective view showing a portion of the web conveyor 100 according to a modified embodiment.

Next, a modified web conveyor 100 according to the embodiment described above is described referring to a drawing. FIG. 9 is a perspective view showing a portion of the web conveyor according to a modified embodiment. Members same as those of the web conveyor 100 according to the embodiment described above are denoted with same signs, and description is focused on differences.

According to the embodiment described above, the edge 111 of the crotch hold bar 110 on the side of the cutting apparatus 300 extends up to a downstream apparatus, that is, up to the non-continuum conveying mechanism 340, whereas according to a modified embodiment, an edge 111 of a crotch hold bar 110 on the side of a cutting apparatus 300 terminates between a downstream roll 232 and the non-continuum conveying mechanism 340.

In this case, a distance D between the edge 111 of the crotch hold bar 110 and an edge 300A of the cutting apparatus 300 on the side of the crotch hold bar 110 is shorter than a width W2 of an absorber 4 along the machine direction MD.

If the distance D is longer than the width W2 of the absorber 4, the waistline portions less rigid than the absorber 4 is located between the edges 111 and 300A before the intermediate web 300 is handed over to the cutting apparatus 300, whereby the vicinity of the leg-surrounding opening portions on the intermediate web 6 may contract in the cross direction CD and thereby a defect such as crease may occur on the intermediate web 6.

OTHER EMBODIMENTS

As described above, details of the present invention are disclosed through various preferable embodiments. However, it should not be understood that description and drawings constituting part of this disclosure limits the present invention. It will be apparent to those skilled in the art that various alternative embodiments, modifications and operational techniques can be made.

For example, an embodiment according to the present invention can be modified. Specifically, although the absorbent article 1 is described as being formed in combination of a pair of waistline portions 10 and crotch portion 20 (so-called three-piece type), it is not limited thereto. Alternatively, the absorbent article 1 may be formed by integrating a pair of waistline portions 10 and crotch portion 20 all together (so-called one-piece type). Moreover, configurations of the absorbent article 1 are not limited to those described in the embodiments, but may be set up appropriately in accordance with any intended use.

Furthermore, although the absorbent article 1 is described as being a pants-type disposable diaper, it is not limited thereto. Alternatively, it may be an article manufactured using the folding step S4 (for example, an open-type diaper or napkin). Moreover, configurations of the absorbent article 1 are not limited to those described on the embodiments, but may be selected suitably according to an intended purpose.

Furthermore, although the webs 61 and 62 are described as having property likely to contract (expand) in the cross direction CD by the waist gather 50, it is not limited thereto. Alternatively, the webs 61 and 62 may be made of a sheet having a self-contracting property.

Furthermore, although the webs 61 and 62 are described as being asymmetrical based on the central line CL, it is not limited to this. Alternatively, the webs 61 and 62 may be asymmetrical with respect to the center line CL.

The method for manufacturing the absorbent article 1 is not limited to those described on the embodiments. Order of steps may be changed (for example, the leg-surrounding portion forming step S3 may be included in the cutting step S6) as far as the absorbent article 1 can be manufactured.

Furthermore, configurations of the joint apparatus 200 and the cutting apparatus 300 are not limited to those described above on the embodiments. For example, the joint apparatus 200 may not be necessarily configured to apply an ultrasonic treatment to the intermediate web 6 but may be configured to apply a heat treatment. Moreover, the cutting apparatus 300 may be configured to cut the intermediate web 6.

Furthermore, although the web conveyor 100 is described as being provided at the region T1 including a location where the intermediate web 6 is handed over from the folding step S4 to the joint step S5 and the region T2 including a location where the intermediate web 6 is handed over from the joint step S5 to the cutting step S6, it is not limited thereto. Alternatively, the web conveyor 100 may be provided at least at the region T1.

Figure 10:
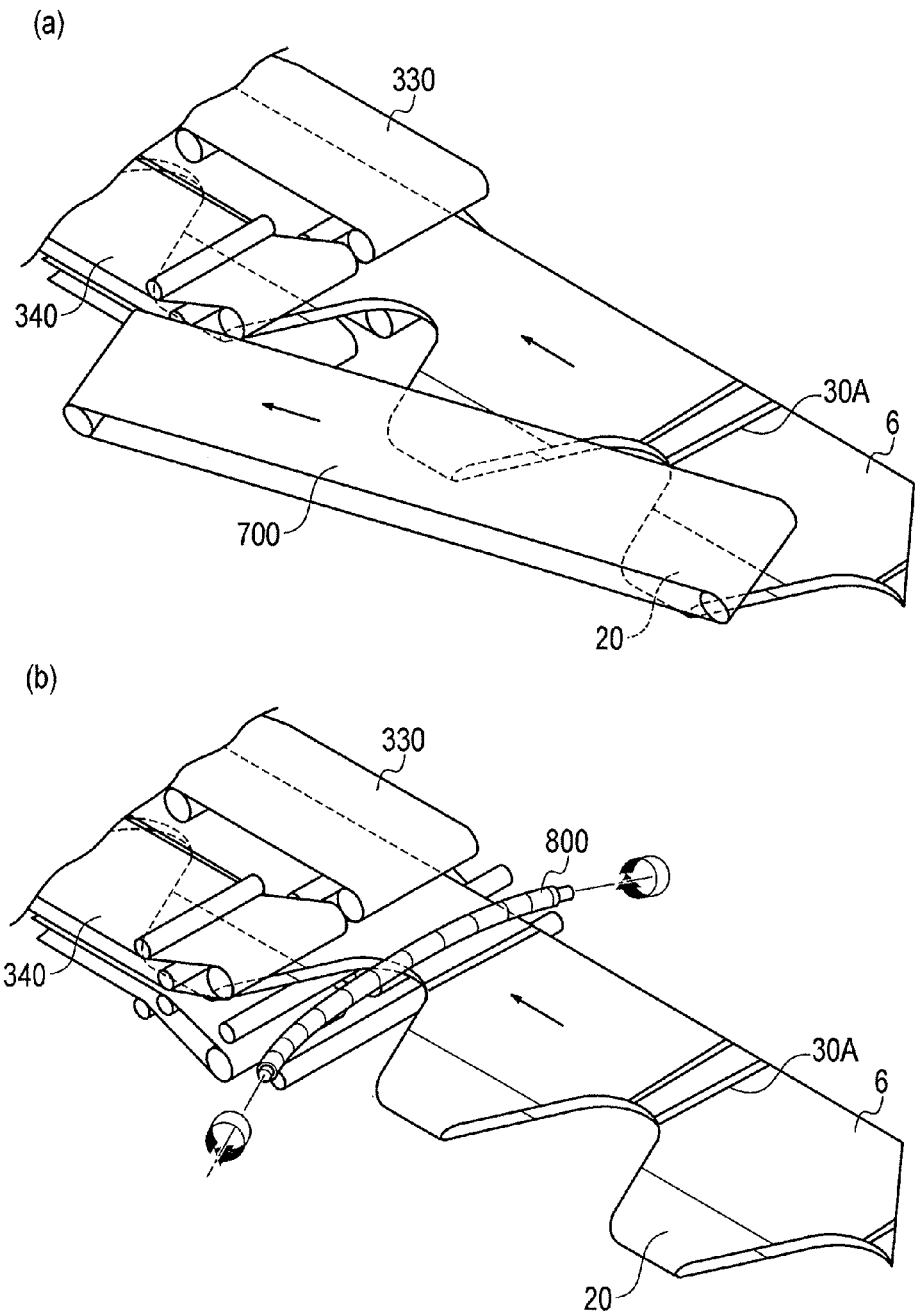
FIG. 10 is a perspective view showing a portion of a web conveyor 100 according to other embodiments.

Furthermore, although the hold mechanism is described as being the crotch hold bar 110 extending along the machine direction MD, it is not limited thereto. Alternatively, the hold mechanism may hold the intermediate web 6 in a conveyable manner with the intermediate web 6 stretched in a direction in which the crotch portion 20 gets away from the waistline portions and along the cross direction CD. For example, as shown in FIG. 10(a), the intermediate web 6 may be held in a conveyable manner by a belt 700 holding the crotch portion 20 in the condition described above. Further alternatively, as shown in FIG. 10(b), the intermediate web 6 may be held in a conveyable manner by an expander roll 800 curbing in the cross direction CD in the condition described above.

Furthermore, although downstream apparatuses are described as being the joint apparatus 200 and the cutting apparatus 300, they are not limited thereto. Obviously, the downstream apparatus may be an apparatus located downstream of the folding apparatus 90.

Furthermore, although the restricting unit 500 is described as being a roller rotatable in the machine direction MD of the intermediate web 6, it is not limited thereto. Instead of the roller, the restricting unit 500 may be a member which is capable of suppressing the crotch hold bar 110 (for example, a projection projecting from an outer peripheral surface of the rotary drum 220).

Furthermore, although the restricting unit 500 is described as being located within an area from the crotch hold bar 110 to the waistline portions of the intermediate web 6, the location is not limited thereto. The restricting unit 500 may be provided within an area from the crotch hold bar 110 to the waistline portions of the intermediate web 6, and within an area from the crotch hold bar 110 to a side of the rotary drum 220 opposite to the waistline portions.

As described above, the present invention obviously includes other various embodiments contained herein. Thus, technical scope of the present invention will be determined by specific invented items according to the scope of claims appropriate from above descriptions.

Note that, the entire content of Japanese Patent Application No. 2009-180203 (filed on Jul. 31, 2009) is incorporated herein by reference.

INDUSTRIAL APPLICABILITY

The present invention can provide a web conveyor and a web conveying method which more surely prevents occurrence of a defect such as a crease on a web even when the web folded into two is conveyed and handed over to another apparatus.

The invention claimed is:

1. A web conveying apparatus configured to convey a web for an absorbent article in a machine direction, said web folded into two in a cross direction orthogonal to the machine direction along a folding line parallel to the machine direction, the web including:
   paired waistline portions continuously extending in the machine direction; and
   crotch portions discontinuous in the machine direction and located between the paired waistline portions,
   the web conveying apparatus comprising:
   a hold mechanism configured to hold the web in a conveyable manner with the web stretched in a direction in which the crotch portions are stretched away from the waistline portions; and
   a conveying mechanism configured to convey the web and to hand over the web to a downstream apparatus provided downstream in the machine direction, while the crotch portions are being held by the hold mechanism;
   wherein
   the downstream apparatus includes a joining apparatus and a cutting apparatus provided downstream of the conveying mechanism in the machine direction, and
   the hold mechanism is configured to hold the web so that a distance in the web in the cross direction from an edge of the waistline portions to an outer edge of the hold mechanism at the downstream apparatus is longer than that at the conveying mechanism.

2. The web conveying apparatus according to claim 1, wherein
   each of the crotch portions is provided with an absorber having a rigidity higher than the waistline portions,
   the absorbers are disposed at predetermined intervals in the machine direction, and
   the conveying mechanism is configured to convey the web so that an airspace in the machine direction between an edge of the hold mechanism on a side near the downstream apparatus and an edge of the downstream apparatus on a side near the hold mechanism is shorter than a width of the absorber in the machine direction.

3. The web conveying apparatus according to claim 1, wherein the hold mechanism is configured to stretch the web from inside of the crotch portions of the folded web.

4. The web conveying apparatus according to claim 1, wherein
the hold mechanism includes a rod-shaped member extending in the machine direction, and
the rod-shaped member is configured to hold the web so that a distance in the web from the edge of the waistline portions in the cross direction to an outer edge of the rod-shaped member in the cross direction is longer at the downstream apparatus than at the conveying apparatus.

5. The web conveying apparatus according to claim 4, further comprising a restricting unit provided within an area from the rod-shaped member to the waistline portions, and configured to restrict a displacement of the rod-shaped member in the cross direction.

6. The web conveying apparatus according to claim 1, further comprising a folding apparatus, wherein the hold mechanism extends along the folding apparatus and the joining apparatus toward the cutting apparatus.

7. A method of conveying a web in a machine direction for an absorbent article folded into two in a cross direction orthogonal to the machine direction along a folding line parallel with the machine direction, the web including:
paired waistline portions continuous in the machine direction; and
crotch portions discontinuous in the machine direction and located between the paired waistline portions, the method comprising:
conveying the web by a hold mechanism in such a manner that the web is stretched in a direction in which the crotch portions get away from the waistline portions; and
conveying the web and handing over the web to a downstream apparatus provided downstream in the machine direction by a conveying mechanism, while the crotch portions are being held by the hold mechanism,
wherein
the downstream apparatus includes a joining apparatus and a cutting apparatus provided downstream of the conveying mechanism in the machine direction, and
a distance in the web in the cross direction from an edge of the waistline portions to an outer edge of the hold mechanism at the downstream apparatus is longer than that at the conveying mechanism.

8. The method according to claim 7, further comprising:
folding the web in the cross direction orthogonal to the machine direction; and
joining the paired waistline portions, the joining performed after the folding,
wherein the hold mechanism is continuously provided at least from the folding to the joining.

9. The method according to claim 7, further comprising restricting a displacement of the hold mechanism in the cross direction by a restricting unit.

10. The method according to claim 7, further comprising:
providing each of the crotch portions with an absorber, the absorber having a rigidity higher than the waistline portions and disposed at predetermined intervals in the machine direction, and
defining an airspace in the machine direction between an edge of the hold mechanism on a side near the downstream apparatus and an edge of the downstream apparatus on a side near the hold mechanism, wherein said airspace is shorter than a width of the absorber in the machine direction.

11. The method according to claim 7, wherein said holding includes stretching the web from inside of the crotch portions of the folded web.

12. The method according to claim 7, wherein
the hold mechanism includes a rod-shaped member extending in the machine direction, and
a distance in the web from the edge of the waistline portions in the cross direction to an outer edge of the rod-shaped member in the cross direction is longer at the downstream apparatus than at the conveying apparatus.

13. The method according to claim 12, further comprising restricting a displacement of the rod-shaped member in the cross direction by a restricting unit provided within an area from the rod-shaped member to the waistline portions.

14. The method according to claim 9, wherein the restricting unit comprises
a first roller having a first shaft oriented in the cross direction, and
a second roller having a second shaft oriented in a direction intersecting with both the machine direction and the cross direction.

15. The method according to claim 14, further comprising
providing a rotary drum rotating together with the restricting unit, and
reducing friction between the rotary drum and the hold mechanism by the first roller provided between the rotary drum and the hold mechanism,
wherein the restricting the displacement of the hold mechanism in the cross direction is performed by the second roller that is rotating about the second shaft while being in contact with the waistline portions of the web.

16. The method according to claim 7, wherein a distance in the web from the edge of the waistline portions to the outer edge of the hold mechanism in the cross direction at the joining apparatus is longer than that at the conveying mechanism and shorter than that at the cutting apparatus.

17. The web conveying apparatus according to claim 1, further comprising a restricting unit configured to restrict a displacement of the hold mechanism in the cross direction,
wherein the restricting unit comprises
a first roller having a first shaft oriented in the cross direction, and
a second roller having a second shaft oriented in a direction intersecting with both
the machine direction and the cross direction.

18. The web conveying apparatus according to claim 17, further comprising a rotary drum, wherein
the rotary drum is rotatable together with the restricting unit,
the first roller is provided between the rotary drum and the hold mechanism for reducing friction between the rotary drum and the hold mechanism, and
the second roller is rotatable about the second shaft while being in contact with the waistline portions of the web for restricting the displacement of the hold mechanism in the cross direction.

19. The web conveying apparatus according to claim 1, wherein a distance in the web from the edge of the waistline portions to the outer edge of the hold mechanism in the cross direction at the joining apparatus is longer than that at the conveying mechanism and shorter than that at the cutting apparatus.

* * * * *